United States Patent [19]
Midler, Jr. et al.

[11] Patent Number: 5,314,506
[45] Date of Patent: May 24, 1994

[54] CRYSTALLIZATION METHOD TO IMPROVE CRYSTAL STRUCTURE AND SIZE

[75] Inventors: Michael Midler, Jr., East Brunswick; Edward L. Paul, Chatham Township, Morris County; Edwin F. Whittington, Linden; Mauricio Futran, Westfield, all of N.J.; Paul D. Liu, Concord, Mass.; Jaanpyng Hsu, Colonia; Shih-Hsie Pan, Princeton Junction, both of N.J.

[73] Assignee: Merck & Co., Inc., Rahway, N.J.

[21] Appl. No.: 793,764

[22] Filed: Nov. 18, 1991

Related U.S. Application Data

[63] Continuation-in-part of Ser. No. 706,682, Jun. 3, 1991, abandoned, which is a continuation-in-part of Ser. No. 538,611, Jun. 15, 1990, abandoned.

[51] Int. Cl.$^5$ .............................................. B01D 9/02
[52] U.S. Cl. ...................................... 23/295 R; 23/299; 423/659; 137/896; 239/421; 239/433; 366/173
[58] Field of Search ............. 137/597, 896; 23/295 R, 23/293 R, 293 A, 293 S, 299; 241/39; 239/420, 421, 433; 366/172, 173, 176; 422/245; 423/659

[56] References Cited

U.S. PATENT DOCUMENTS

| | | |
|---|---|---|
| 2,751,335 | 6/1956 | Carver et al. ................... 23/293 R |
| 3,622,496 | 11/1971 | Biribauer et al. ................. 208/35 |
| 4,567,912 | 2/1986 | Levine ............................ 137/606 |
| 4,663,433 | 5/1987 | Pyles et al. ..................... 528/496 |
| 4,783,008 | 11/1988 | Ikeuchi et al. ................... 239/421 |
| 4,915,302 | 4/1990 | Kraus et al. ..................... 239/14.2 |
| 4,952,224 | 8/1990 | Lilakos ............................ 62/534 |
| 5,011,293 | 4/1991 | Roop et al. ...................... 366/173 |
| 5,074,671 | 12/1991 | Roueche et al. .................. 366/172 |

FOREIGN PATENT DOCUMENTS

| | | |
|---|---|---|
| 157562 | 10/1985 | European Pat. Off. . |
| 0344898A1 | 4/1990 | European Pat. Off. . |
| 393963 | 10/1990 | European Pat. Off. . |
| 3126854 | 1/1983 | Fed. Rep. of Germany . |

OTHER PUBLICATIONS

R. Pohorecki & J. Baldyga, The Use of a New Model of Micromixing for Determination of Crystal Size in Precipitation, Chem. Eng. Sci. 38 79–83 vol. 38, No. 1 Jan. 1983.

J. Garside and N. S. Tavare, Mixing, Reaction and Precipitation: Limits of Micromising in an MSMPR Crystallizer, Chem. Eng. Sc., vol. 40 No. 8 Aug. 1985.

A Mersmann and M. Kind, Chemical Engineering Aspects of Precipitation from Solution, Chem. Eng. Technol, 11, pp. 264–276 (1988), Aug. 1904.

M. Midler, et al., Abstract, Annual Meeting American Inst. Chem. Eng., San Francisco, Calif. (Nov. 5, 1989).

P. Liu, et al., (abstract) "The Use of Continuously Impinging Jets to Control Crystallization and Particle Size . . . ", *Extended Abstracts, American Institute of Chemical Engineers, 1990 Annual Meeting*, paper No. 66B, available to attendees Nov. 11, 1990, at Chicago, IL.

A. J. Mahajan, et al., (abstract) "Rapid Precipitation of Amino Acids", *Extended Abstrcts, American Institute of Chemical Engineers, 1991 Annual Meeting*, paper No. 74e, available to attendees Nov. 17, 1991, at Los Angeles, Calif.

*Primary Examiner*—Michael Lewis
*Assistant Examiner*—Timothy C. Vanoy
*Attorney, Agent, or Firm*—Joseph F. DiPrima; Robert J. North; Carol S. Quagliato

[57] ABSTRACT

Impinging fluid jet streams are used in a continuous crystallization process to achieve high intensity micromixing of fluids so as to form a homogeneous composition prior to the start of nucleation. This process permits direct crystallization of high surface area particles of high purity and stability.

28 Claims, 4 Drawing Sheets

CRYSTALLIZATION METHOD TO IMPROVE CRYSTAL STRUCTURE AND SIZE

RELATED APPLICATION

This application is a continuation-in-part of co-pending U.S. application Ser. No. 706,682, filed Jun. 3, 1991, which itself is a continuation-in-part of U.S. application Ser. No. 07/538,611, filed on Jun. 15, 1990, and now abandoned.

BACKGROUND OF THE INVENTION

Crystallization from solution of pharmaceutically active compounds or their intermediates is the typical method of purification used in industry. The integrity of the crystal structure, or crystal habit, that is produced and the particle size of the end product are important considerations in the crystallization process.

High bioavailability and short dissolution time are desirable or often necessary attributes of the pharmaceutical end product. However, the direct crystallization of small sized, high surface area particles is usually accomplished in a high supersaturation environment which often results in material of low purity, high friability, and decreased stability due to poor crystal structure formation. Because the bonding forces in organic crystal lattices generate a much higher frequency of amorphism than those found in highly ionic inorganic solids, "oiling out" of supersaturated material is not uncommon, and such oils often solidify without structure.

Slow crystallization is a common technique used to increase product purity and produce a more stable crystal structure, but it is a process that decreases crystallizer productivity and produces large, low surface area particles that require subsequent high intensity milling. Currently, pharmaceutical compounds almost always require a post-crystallization milling step to increase particle surface area and thereby improve their bioavailability. However, high energy milling has drawbacks. Milling may result in yield loss, noise and dusting, as well as unwanted personnel exposure to highly potent pharmaceutical compounds. Also, stresses generated on crystal surfaces during milling can adversely affect labile compounds. Overall, the three most desirable end-product goals of high surface area, high chemical purity, and high stability cannot be optimized simultaneously using current crystallization technology without high energy milling.

One standard crystallization procedure involves contacting a supersaturated solution of the compound to be crystallized with an appropriate "anti-solvent" in a stirred vessel. Within the stirred vessel, the anti-solvent initiates primary nucleation which leads to crystal formation, sometimes with the help of seeding, and crystal digestion during an aging step. Mixing within the vessel can be achieved with a variety of agitators (e.g., Rushton or Pitched blade turbines, Intermig, etc.), and the process is done in a batchwise fashion.

When using current reverse addition technology for direct small particle crystallization, a concentration gradient can not be avoided during initial crystal formation because the introduction of feed solution to anti-solvent in the stirred vessel does not afford a thorough mixing of the two fluids prior to crystal formation. The existence of concentration gradients, and therefore a heterogeneous fluid environment at the point of initial crystal formation, impedes optimum crystal structure formation and increases impurity entrainment. If a slow crystallization technique is employed, more thorough mixing of the fluids can be attained prior to crystal formation which will improve crystal structure and purity, but the crystals produced will be large and milling will be necessary to meet bioavailability requirements.

Another standard crystallization procedure employs temperature variation of a solution of the material to be crystallized in order to bring the solution to its supersaturation point, but this is a slow process that produces large crystals. Also, despite the elimination of a solvent gradient with this procedure, the resulting crystal characteristics of size, purity and stability are difficult to control and are inconsistent from batch to batch.

The novel process of this invention utilizes impinging jets to achieve high intensity micromixing in the crystallization process. High intensity micromixing is a well known technique where mixing-dependent reactions are involved. Feeding strategies as they relate to precipitation were addressed by Mersmann, A. and Kind, M., *Chemical Engineering Aspects of Precipitation from Solution*, Chem. Eng. Technol., V. 11, p. 264 (1988). Notable among other papers recently addressing the effect of micromixing in reaction processes are Garside, J. and Tavare, N. S., *Mixing, Reaction and Precipitation: Limits of Micromixing in an MSMPR Crystallizer*, Chem. Eng. Sci., V. 40, p. 1485 (1985); Pohorecki, R. and Baldyga, J., *The Use of a New Model of Micromixing for Determination of Crystal Size in Precipitation*, Chem. Eng. Sci., V. 38, p. 79 (1983). However, the use of high intensity micromixing is not the norm in current crystallization technology where no chemical reaction is involved.

Impinging jets are used for micromixing routinely in reaction injection moulding (RIM) technology in the plastics industry but not for the purpose of causing crystallization. The use of an impinging jet device in a crystallization process to achieve intense micromixing is novel. Whether feed material is relatively pure or impure, the use of impinging jets results in crystal characteristics superior to those that result from standard crystallization methods.

Now with the present invention there is provided a method for crystallization of pharmaceutical compounds or their intermediates which directly produces high surface area end product crystals with greatly improved stability and purity and thereby eliminates the need for subsequent high intensity milling to meet bioavailability requirements. By removing the need for milling, the novel jet process avoids associated problems of noise and dusting, cuts yield loss, and saves the time and extra expense incurred during milling. It also removes an extra opportunity for personnel contact with a highly potent pharmaceutical agent, or for adverse effects on labile compounds. The small particle size attained with the jet process is consistent within a single run and as shown in Table 1, results are reproducible between runs. Reproducibility is an attribute of this process that is not common to "reverse addition" methods typically used to produce small crystals.

The pure, high surface area particles that result from the jet process also display superior crystal structure when compared to particles formed via standard slow crystallization plus milling methods using the same quality and kind of feed compound. Improvements in crystal structure result in decreases in decomposition rate and therefore longer shelf-life for the crystallized product or a pharmaceutical composition containing the crystallized material. As shown in Table 2, the material produced by the jet process exhibits more consistent accelerated stability results than that produced by the conventional batch process.

The purity of crystallized material produced from the jet process is superior to that from standard reverse addition direct small particle crystallization, as demonstrated with simvastatin using high performance liquid chromatography (HPLC) in Table 3. Standard slow batch crystallization affords product purity comparable to that afforded by the jet process, but the jet process is superior because, as noted above, in addition to high purity, it also provides higher quality crystal habit and increased particle surface area thereby eliminating the need for milling.

Jet process crystallization is suited for continuous processing. Standard crystallization methods are generally run in a batchwise fashion. Continuous processing affords two advantages. First, the same amount of feed compound can be crystallized in significantly less volume via continuous processing than would be possible using a batch by batch method. Second, continuous processing enhances reproducibility of results because all the material crystallizes under uniform conditions. Such uniformity is not possible using batch methods in which concentration, solubility and other parameters change with time.

TABLE 1

JET CRYSTALLIZED SIMVASTATIN

| Batch | Surface Area $(m^2/g)$ at 45–55° C. |
|---|---|
| 1 | 3.37* |
| 2 | 2.57* |
| 3 | 2.88* |
| 4 | 3.56* |
| 5 | 3.35 |
| 6 | 2.55 |
| Mean: | 3.05 |
| Standard Deviation: | 0.40 |

*Run at 50–51° C.

TABLE 2

60° C. ACCELERATED STABILITY TEST

| Batch | Surface Area | Weeks (at 60° C.) | | | | | Temp. °C. |
|---|---|---|---|---|---|---|---|
| | | 0 | 1 | 2 | 4 | 6 | 8 | |
| JET CRYSTALLIZED SIMVASTATIN | | | | | | | | |
| 1 | 2.4 | 98.7 | 99.4 | 96.8 | 95.1 | | 97.2 | 68 |
| 2 | 4.0 | 98.9 | 92.5 | 93.3 | 98.1 | | 95.1 | 55 |
| 3 | 5.5 | 99.3 | 96.5 | 88.5 | 93.4 | | 85.7 | 55 |
| 4 | 4.6 | 98.8 | 95.1 | 96.4 | 86.0 | | 80.1 | 55 |
| SLOW BATCH CRYSTALLIZED SIMVASTATIN (MILLED) | | | | | | | | |
| 1 | 3.0 | 98.9 | 95.5 | 95.7 | 95.0 | 95.0 | | * |
| 2 | 3.3 | 99.1 | 94.9 | 94.3 | 83.6 | 95.0 | | * |
| 3 | 2.6 | 99.0 | 98.2 | 95.9 | 93.0 | | 93.5 | * |
| 4 | 2.7 | 99.2 | 98.4 | 95.3 | 95.4 | | 82.8 | * |
| 5 | | 99.7 | 98.3 | 98.0 | 81.3 | | 36.6 | * |
| 6 | | 99.2 | 94.0 | 89.0 | 77.8 | | 34.0 | * |

*Heat-cool process used.

TABLE 3

| Simvastatin Crystallization Method* | Temp. (°C.) | HPLC Purity (Weight %) | 969 Impurity** (Weight %) |
|---|---|---|---|
| Continuous Impinging Jets | 50 | 99.0 | <0.1 |
| Continous Impinging Jets | 25 | 98.6–99.0 | 0.2–0.4 |
| Batch Reverse | 25 | 98.7 | 0.7 |

TABLE 3-continued

| Simvastatin Crystallization Method* | Temp. (°C.) | HPLC Purity (Weight %) | 969 Impurity** (Weight %) |
|---|---|---|---|
| Addition | | | |
| Slow Batch Process | | 99.0 | <0.1 |
| Product Specification | | >98.5 | <0.5 |

*50:50 Volumetric ratio of MeOH:H₂O used with impinging jet method; final volumetric ratio of 50:50 MeOH:H₂O used with reverse addition and slow batch methods.
**Open ring form of simvastatin.

SUMMARY OF THE INVENTION

This invention concerns a process for crystallization. More particularly, this invention relates to the use of impinging jets to achieve high intensity micromixing of fluids so as to form a homogeneous composition prior to the start of nucleation in a continuous crystallization process. Nucleation and precipitation can be initiated by utilizing the effect of temperature reduction on the solubility of the compound to be crystallized in a particular solvent (thermoregulation), or by taking advantage of the solubility characteristics of the compound in solvent mixtures, or by some combination of the two techniques.

The novel process of this invention provides for the direct crystallization of high surface area particles of high purity and stability.

BRIEF DESCRIPTION OF THE DRAWINGS

Two embodiments of the invention have been chosen for purposes of illustration and description, and are shown in the accompanying drawings forming a part of the specification wherein.

DETAILED DESCRIPTION OF THE INVENTION

Figure 1:
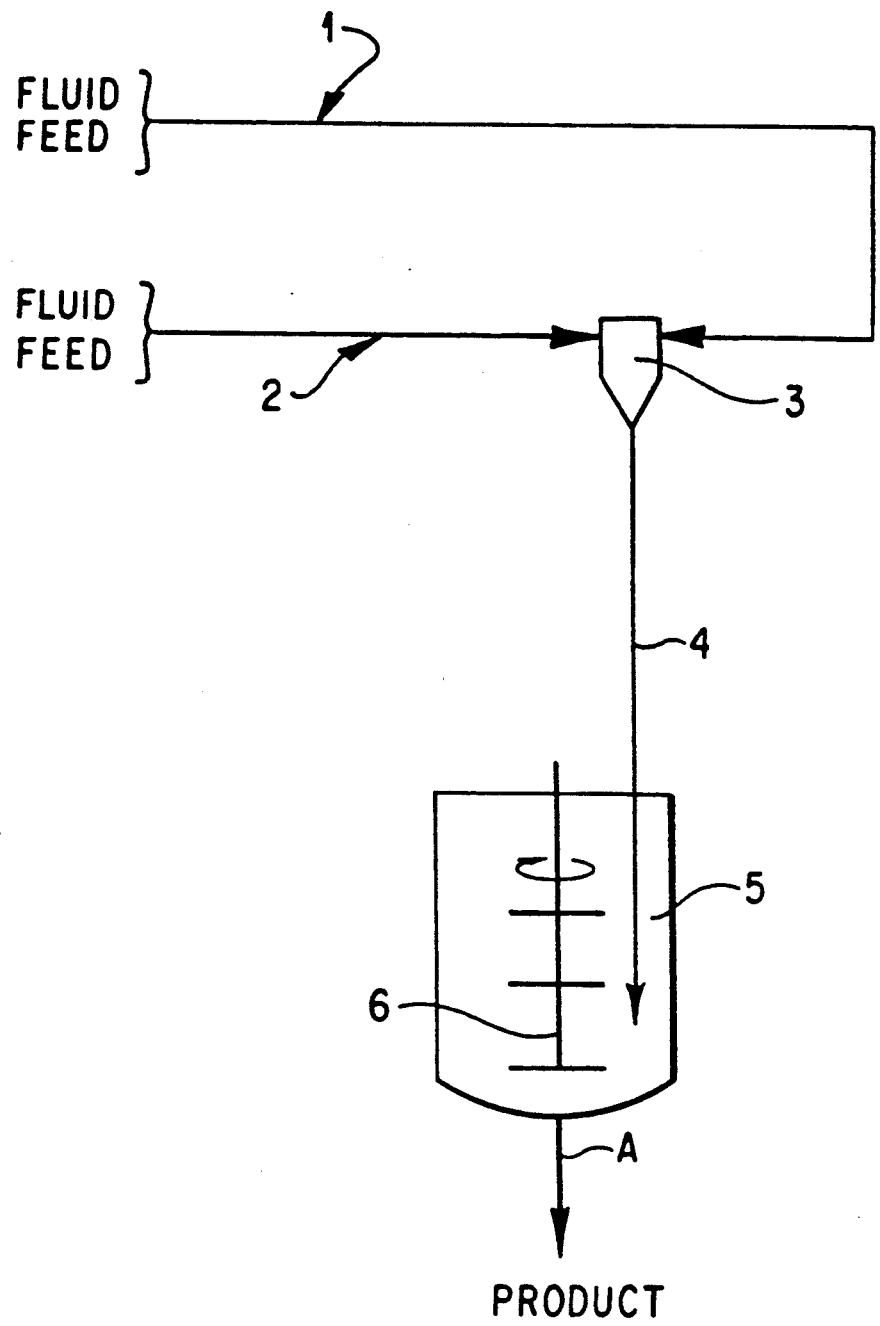
FIG. 1 is a schematic diagram showing a crystal production system depicting the jet chamber 3, the transfer line 4, the stirred vessel 5, the agitation device 6 and the entry point of two fluids 1 and 2 into the system.
Figure 5:
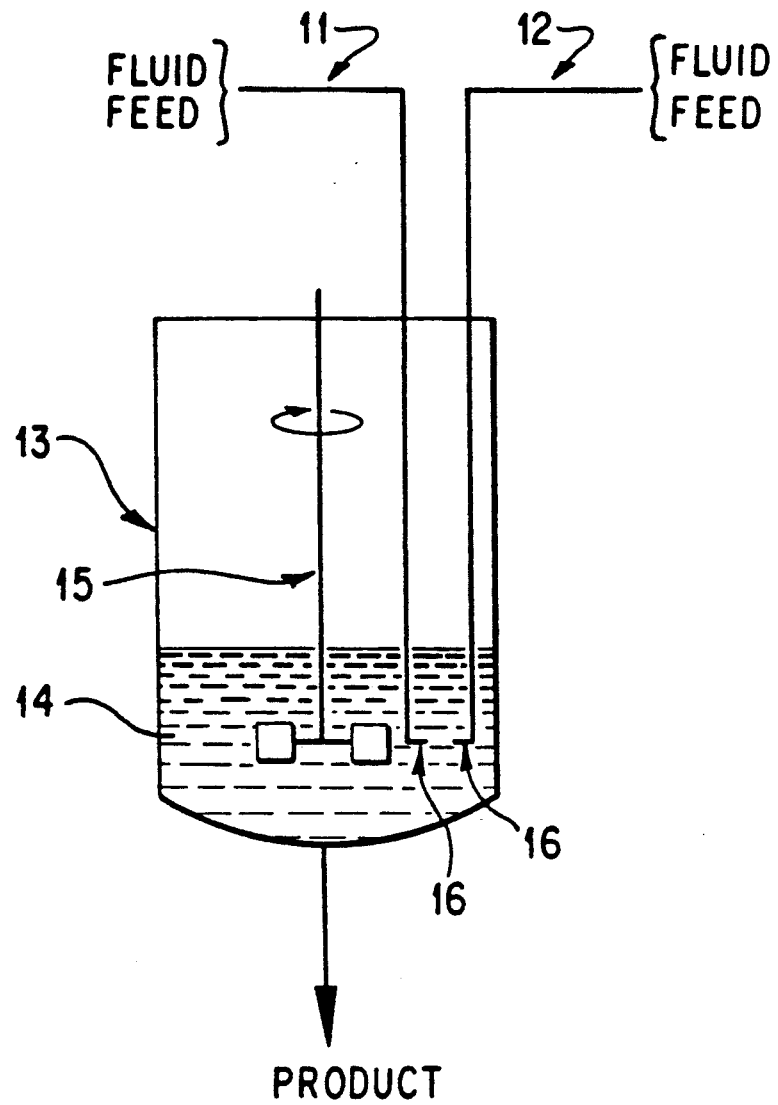
FIG. 5 is a schematic diagram showing a crystal production system depicting two fluids, 11 and 12, entering directly into the stirred vessel 13 containing liquid 14 (the liquid being solvent and/or anti-solvent) where the jets 16 emit fluid jetstreams that impinge and micromix near the effluent stream of the impeller 15.

The novel process of this invention involves the use of jets to create impinging fluid jet streams and thereby achieve high intensity micromixing of the fluids prior to nucleation in a crystallization process. Two or more jets may be used to micromix two or more fluids. Preferably, two jets are used to micromix two fluids. When using two jets, preferably the two impinging jet streams should be substantially diametrically opposed to each other, i.e., they should be at or close to a 180 degree angle to each other from an overhead view. FIG. 1 shows one embodiment of this invention wherein two jets are employed; fluids 1 and 2 enter the jet chamber 3 where micromixing takes place. FIG. 5, shows another embodiment of this invention, wherein 2 jets are employed and the jetstreams impinge and micromix directly in the stirred vessel 13. As used herein, the terms stirred vessel and age vessel have the same meaning and are interchangeable.

The two fluids used in the novel process of this invention can be of different solvent composition, one fluid being a solution of the compound to be crystallized in a suitable solvent or combination of solvents ("feed solution"), and the other fluid being a suitable solvent or combination of solvents capable of initiating that compound's precipitation from solution ("anti-solvent"), chosen for its relatively low solvation property with respect to that compound. Such solvents and anti-solvents can include but are not limited to methanol, ethyl acetate, halogenated solvents such as methylene chloride, acetonitrile, acetic acid, hexanes, ethers, and water.

Or, the two fluids used in the process can both be solutions of the compound to be crystallized in the same suitable solvent or combination of solvents but each at a different temperature, and nucleation/precipitation can be initiated by instantaneous temperature reduction. The temperature and composition of each solution are chosen so that 1) no material will crystallize upstream of the impinging jets, and 2) sufficient supersaturation will be developed in the impinging jets to cause nucleation. Micromixing creates temperature and compositional uniformity throughout the mixture prior to the start of nucleation.

The fluids used in the process can also contain a small amount of a suitable surfactant which may alleviate agglomeration which might occur during the jet mix crystallization process. Thus, one, several or all of the fluids employed may contain a surfactant as less than 1% of its volume. The preferred amount of the surfactant is between 0.05% and 1% of the volume of the fluid. Since such a surfactant may be incorporated in the crystalline compound the surfactant should be chosen which will be innocuous to the eventual use of the crystalline compound. Suitable surfactants which may be included in the fluids employed in the process include but are not limited to Triton X-100, sodium dodecyl sulfate, Witconol-14F, Enthos D70-30C and the like.

The following is a list of compounds that have been successfully crystallized to meet particle size and purity specifications using the present invention: simvastatin, lovastatin (crude and pure), omeprazole, PROSCAR ® ((5α,17β)-(1,1-dimethylethyl)-3-oxo-4-azaandrost-1-ene-17-carboxamide), diltiazem malate, 17β-benzoyl-4-aza-5α-androst-1-ene-3-one, 4"-epi-acetylamino-avermectin $B_1$, [trans-(−)]-2-[[3-methoxy-2-propoxy-5-[tetrahydro-5-(3,4,5-trimethoxyphenyl)-2-furanyl]phenyl]-sulfonyl]ethanol (DevLab, England). However, this is not an exhaustive list of all the compounds that can be used with the present invention.

After micromixing in a jet chamber, the material leaves the jet chamber as depicted in FIG. 1, travels into a stirred vessel 5 either directly or via a transfer line 4, and after an appropriate age time, the product suspension flows out of the vessel as indicated by arrow A. Another embodiment of this invention involves the micromixing of two impinging jetstreams directly in the stirred vessel without the use of a jet chamber or transfer line, as depicted in FIG. 5. For the crystallization of simvastatin, the preferred method is for two jetstreams to impinge directly in the stirred vessel. Once the material leaves the stirred vessel, appropriate recovery techniques are used to isolate the product crystals. The material preferably flows through the system in a continuous process, although it is possible to hold up the process in a batchwise fashion at the stirred vessel-aging step given a vessel of sufficient volume.

Figure 2:
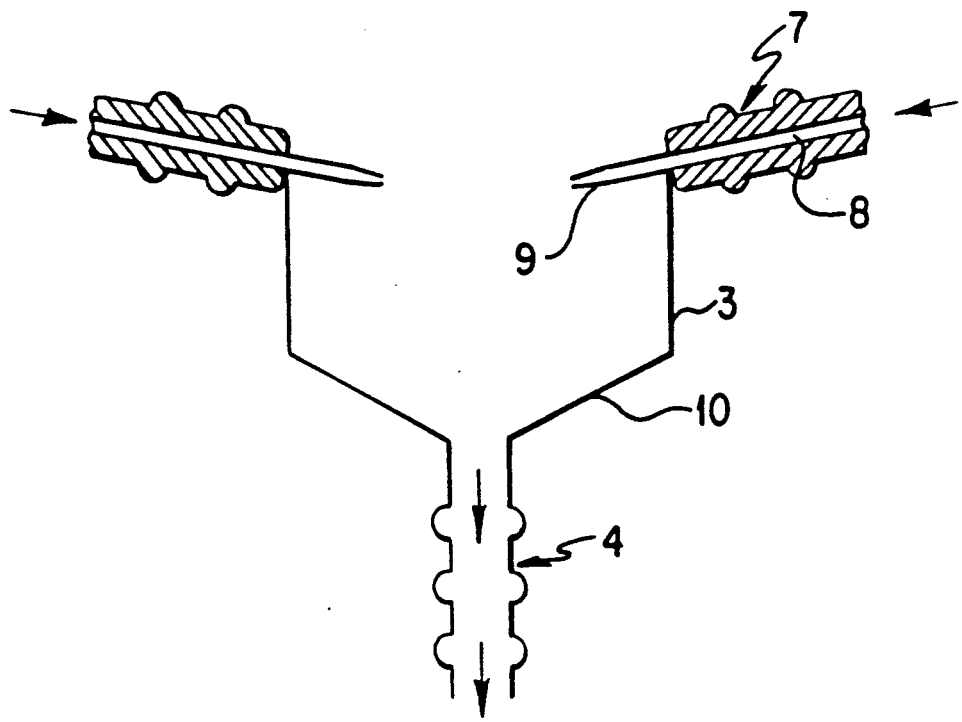
FIG. 2 is an enlarged sectional view of jet chamber 3 showing an arrangement for impinging jet introduction of two fluids into the system.
Figure 3:
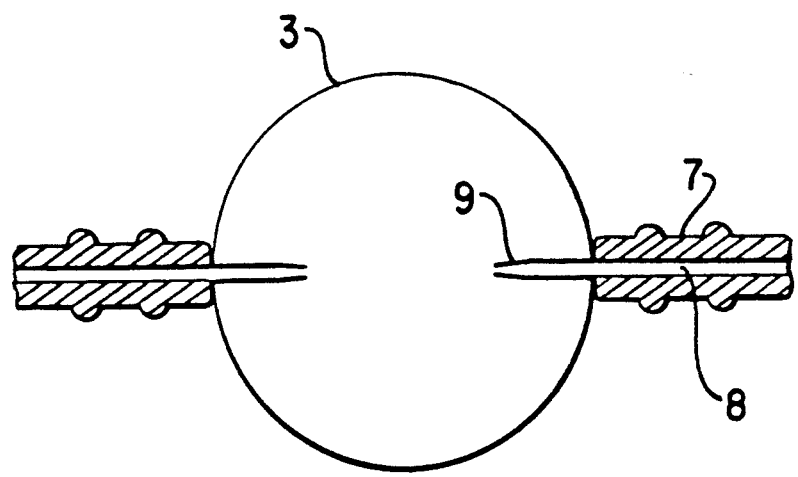
FIG. 3 is an overhead view of the jet chamber 3.

As shown in FIG. 2 and FIG. 3, the jet chamber 3 is preferably cylindrical in shape and as shown in FIG. 2 the jet chamber 3 preferably has a floor 10 which slopes downward in a conical shape toward the floor's center which is open to a connecting transfer line 4 or directly into a stirred vessel or other appropriate container. The diameter and cylinder wall height of the chamber can vary according to scale needs.

Regardless of the number of jets used, the jet nozzles should be placed so that the fluid streams they emit will impinge, either inside the jet chamber or directly in the stirred vessel. The fluid jets must impinge to create an immediate high turbulence impact; concentric or converging jets generally create insufficient turbulence to achieve the required micromixing. When two jets are used with a jet chamber, as shown in FIG. 2 and FIG. 3, the two jet nozzles 7 are preferably arranged so that they are substantially diametrically opposed to each other with their outlet tips directed to face each other; i.e., the two jet nozzles are at or close to a 180 degree angle to each other from an overhead view. Preferably, each jet outlet nozzle can have a slight downward angle from the horizontal of about 10 degrees to help the flowing material move down and out of the chamber.

Likewise, two jet nozzles placed directly inside the stirred vessel are preferably arranged so that they are substantially diametrically opposed to each other with their outlet tips directed to face each other. When the jet nozzles are so placed, each nozzle can have a slight upward or downward angle from the horizontal of from 0 degrees up to about 15 degrees, but preferably the two nozzles have just enough downward angle from the horizontal (ca. 13 degrees) to ensure that the fluid stream of one will not enter the outlet hole of the opposite nozzle.

One jet nozzle is used to transport one of the two fluids from an external source into the chamber and the other jet is used to similarly transport the other fluid. The distance between the nozzle tips inside the jet chamber or stirred vessel should be such that the hydrodynamic form of each fluid jet stream remains essentially intact up to the point of impingement. Therefore, the maximum distance between the nozzle tips will vary depending on the linear velocity of the fluids inside the jet nozzles. To obtain good results for generally non-viscous fluids, linear velocity in the jet nozzles should be at least about 5 meters/sec., more preferably above 10 meters/sec., and most preferably between about 20 to 25 meters/sec., although the upper limit of linear velocity is only limited by the practical difficulties involved in achieving it. Linear velocity and flow rate can both be controlled by various known methods, such as altering the diameter of the entry tube 8 and/or that of the nozzle outlet tip 9, and/or varying the strength of the external force that moves the fluid into and through the nozzle. Each jet apparatus can be manipulated independently to attain a desired final fluid composition ratio. When the desired flow ratio of one jet to the other differs from unity, preferably the difference is compensated for by appropriate sizing of the entry tubes. For example, if a 4:1 volumetric ratio of feed solution to anti-solvent is desired, the entry tube delivering feed solution should be twice the diameter of the entry tube delivering anti-solvent. When the jetstreams impinge inside a jet chamber, residence time for the fluid inside the jet chamber is typically very short, i.e., less than ten seconds.

A transfer line 4 as shown in FIG. 1 may or may not be used to deliver the fluid mixture into a stirred vessel 5 from the jet chamber. Solvent, anti-solvent or mixtures thereof optionally containing seed and optionally heated to attain optimum crystallization results can be put inside the stirred vessel FIG. 1 (5), FIG. 5 (13) at the start of the process before the micromixed fluids enter the stirred vessel; this technique is especially preferred when the jetstreams impinge directly in the stirred vessel. Crystal digestion (Ostwald ripening, improvement of surface structure) takes place inside the stirred vessel.

Stirring in the vessel is provided by standard agitators 6, preferably Rushton turbines, Intermig impellers, or other agitators suitable for stirring a slurry suspension. Any impeller providing good circulation inside the vessel may be used. However, when the jetstreams are arranged to impinge directly inside the stirred vessel, an agitator that does not interfere with the space occupied by the impinging jetstreams inside the vessel is preferred, especially, e.g., a Rushton turbine. As depicted in FIG. 5, impinging jetstreams inside the vessel are most preferably placed in the effluent stream of the agitator, and the height of the liquid in the stirred vessel when operated in continuous mode (i.e., flow in equals flow out, constant volume maintained), is most preferably between about two to four times the height of the impeller.

The crystallization is preferably run in a continuous process and the appropriate residence time for the completion of crystal digestion is attained by adjusting the volume capacity of the stirred vessel, but the mixture can be held up in the vessel for any desired length of age time if batchwise processing is desired. For example, during simvastatin crystallization crystal digestion is complete within about 5 minutes and a vessel volume of roughly 5 liters is sufficient for a residence time of 5 minutes with a material flow of about 1 liter per minute. PROSCAR ® is similar to simvastatin with respect to age time. In some instances when the fluids impinge and micromix inside a jet chamber, crystallization conditions may be optimized so that crystal precipitation and growth are completed within the transfer line itself, or even before entering the transfer line, and the crystals may be directly collected, bypassing any age time in the stirred vessel.

Manual seeding can be done at any point in the system, e.g., in the stirred vessel, the transfer line or the jet chamber itself. In some situations, the continuous jet process may be "self-seeding", i.e., the first crystals to form inside the jet chamber (if used), the transfer line (if used) or the stirred vessel (if used) serve as seed for the material that flows through thereafter.

Figure 4:
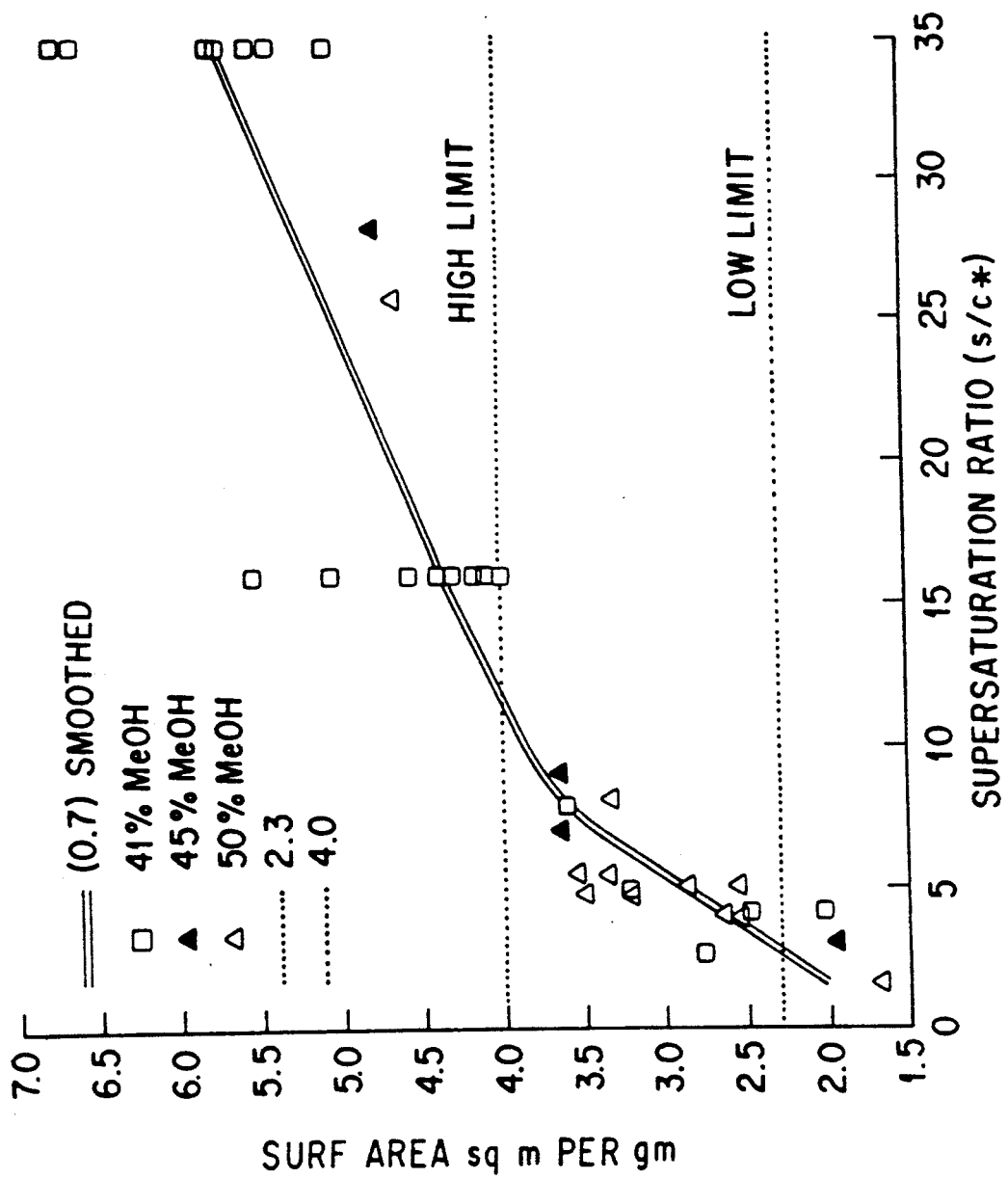
FIG. 4 shows particle surface area as a function of supersaturation ratio using the jet crystallization process with simvastatin.

The micromixed material must be highly supersaturated to attain the beneficial results of the jet crystallization process. Aside from thermoregulated initiation of nucleation, temperature variation also affects product results when anti-solvent is used to initiate nucleation because of its effect on supersaturation. Generally, good results can be achieved for pharmaceutical compounds using a volumetric ratio of feed solution to anti-solvent that provides a high degree of supersaturation in the jet chamber in a temperature range of about 24° C. to 70° C., although temperature height is limited only by the chosen solvent's boiling point and the compound's decomposition range. Temperatures above ambient may give improved product characteristics. As an example, optimum results with regard to end product surface area, purity and stability are achieved for simvastatin by running the crystallization at an elevated temperature of at least 55° C., more preferably in the range of 60 to 70° C., and most preferably at 65 to 68° C., in a 41:59 volumetric mixture of $MeOH:H_2O$. In this case, the composition in the impinging jetstreams is 50:50 $MeOH:H_2O$, and the composition in the age tank is brought to 41:59 $MeOH:H_2O$ by a separate, additional water injection (not through the impinging jet) directly into the stirred vessel. A 75:25 volumetric mixture of $MeOH:H_2O$ used at room temperature produces crystals essentially the same as those from conventional batchwise crystallization, i.e, they require milling. A 41:59 volumetric mixture of $MeOH:H_2O$ used at room temperature results in particles with average surface area above the desirable range and decreased purity as shown in FIG. 4. Ambient temperature operation using the jet process provides sufficiently good results for PROSCAR ® and therefore elevated temperatures are not necessary.

The following examples are given for the purpose of illustrating the present invention and should not be construed as limitations on the scope or spirit of the instant invention.

EXAMPLE 1

Crystallization of PROSCAR ®

100 Grams of PROSCAR ® dissolved in 600 ml. of glacial acetic acid; once dissolution was complete, 400 ml. deionized water was added. The solution was filtered through a 0.2 micron membrane into a blow can. The blow can outlet was connected to a 1/16 in. OD jet nozzle (0.052 in. ID). 5.5 Liters of deionized water was filtered through a 0.2 micron membrane into a second blow can, and its outlet connected to a ⅛ in. OD jet nozzle (0.0938 in. ID). Each blow can was pressurized to ca. 90 psi with regulated nitrogen. The impinging jets were started simultaneously. The desired flow rate of the acetic acid solution was 0.2 gpm (linear velocity ca. 550 meters/min.) and the desired flow rate of 100% $H_2O$ was 1.1 gpm (linear velocity ca. 930 meters/min.). The effluent slurry was collected from the mixing chamber in a 12L round-bottom flask equipped with a paddle agitator. A minimum age time of two minutes was required to complete crystal digestion. The solids were filtered, water washed, then dried.

Crystals were 10 to 20 microns in diameter and 1 micron thick, in the form of flakes; specification is 95% <smaller than 25 microns.

EXAMPLE 2

100 Grams of simvastatin were dissolved in 1400 ml. methanol, and the solution heated to approximately 55° C. Deionized water (1400 ml.) was heated to approximately 55° C. The heated water was fed to one blow can and the heated methanol solution was fed to a second blow can. Each blow can outlet was connected to a 1 mm. ID jet nozzle. Each blow can was pressurized to 25–35 psi, and impinging jets were started simultaneously. The flow from each jet was 1.1 liter/min. (linear velocity ca. 23 meters/sec.).

The jet chamber was approximately 2 inches in diameter and 1 inch high with a conical bottom outlet. Effluent from this chamber was directed to a 4 liter beaker (approx. 6 inches diameter). The beaker contained 2.5 grams simvastatin seed (dry-surface area 2.5 to 6 sq m/gm), and was agitated at 300 RPM by three Ekato Intermig impellers, each 3.5 inches in diameter. When the cans were empty (75 seconds), they were vented. Aging (agitation at 300 RPM, no cooling) took place in the beaker for 5 to 20 minutes. The contents were then cooled with the same agitation to less than 30° C. by immersion in an ice bath. Contents were then filtered and tray dried (40° C. at 28-30 in. Hg vacuum with slight nitrogen sweep) for 12 to 16 hours.

The resultant dry solid (88-99 grams) had a surface area of 3.1 +/−0.4 square meters per gram. Mother liquor losses were 1-2%, the remaining yield being held up in the apparatus. Product could be used to seed future batches without further treatment.

EXAMPLE 3

Crystallization of Simvastatin, 66-68° C.

The crystallization of Example 2, with the following modifications:

(1) temperature in the jet impingement zone and in the 5 to 20 minute age was raised to 66-68° C., by preheating the methanol feed solution to 55° C. and the water feed to 85° C.; and (2) final age tank solvent composition was reduced to 41% methanol by suspension of the initial 2.5 gram seed charge in 600 ml deionized water at 70° C.

The final product was similar in particle size, surface area and appearance to the product from Example 2. However, storage stability (60° C.) was improved from very good (Example 2) to outstanding (Example 3), implying a higher order of crystallinity.

EXAMPLE 4

Crystallization of Simvastatin. Immersed Jets

The crystallization of Example 3, with the modification that the impinging jets were submerged, without containment, inside the agitated age vessel near the effluent stream of the impeller. To accommodate the immersed jets, a 6-liter baffled battery jar (cylindrical), 8¼ inches in diameter and 10 inches high, was agitated by a 3 inch diameter Rushton turbine. The impinging jets were located near the horizontal plane of the impeller, 1 to 2 inches from the impeller's outer edge.

The final product was essentially identical with that of Example 3. Caking of amorphous solid on the wall of the jet chamber, which occurs in extended runs in Examples 2 and 3, was eliminated because there was no containment wall around the jets.

EXAMPLE 5

Crystallization of Lovastatin 38.0 Grams of lovastatin were added to 1260 ml methanol and 140 ml deionized water. The mixture was heated to 55° C. with agitation (magnetic stirrer in closed Erlenmeyer flask). Activated carbon (12.7 g, Calgon type APA 12×40) was added, the mixture stirred at 55° C. and hot filtered. The filtrate was reheated to 55° C. (when necessary) and added quickly to a blow can attached to one impinging jet device nozzle (1.0 mm diameter). 538 Milliliters of 60° C. deionized water was added to another blow can connected to the opposing jet (0.5 mm diameter). Both cans were pressurized to 25-30 psig and the liquids fed to the respective jets, completed in 1 minute, 45 seconds. The agitated beaker (same as Example 1) was aged at the jet outlet temperature (43° C.) for 5 minutes, cooled with stirring to less than 30° C., and filtered and dried.

The final product was fine needles with acceptable surface area 1.6 $m^2$/gm. Purity was equal to that from conventional seeded crystallization.

EXAMPLE 6

Crystallization of Omeprazole with Triton X-100

4 Grams of omeprazole was dissolved in 250 mL of methanol at 42° C.; once dissolution was complete, 0.25 mL of concentrated ammonium hydroxide was added to bring the pH of the solution to 8.5-9.0 The solution was filtered into a blow can. The blow can outlet was connected to a jet which had a 0.991 mm ID nozzle. A solution of approximately 0.3 mL of Triton X-100 in 250 mL of water at 42° C. was charged in a second blow can which was connected to a similar jet nozzle. The jet nozzles were separated by 0.5 inches. Both blow cans were maintained at 42° C.–45° C. prior to release.

The receiving vessel was charged with 200 mL of water, which was warmed to 42° C. 0.3 mL of Triton X-100 and 0.45 grams of milled omeprazole were added to the water and the mixture was slowly agitated.

The blow cans were pressurized to approximately 20 psig with regulated nitrogen. The impinging jets of the blow cans were started simultaneously with the flow rates of each stream approximately 0.7 L/minute (linear velocity approximately 15 m/sec.). After the jet mixing was complete, 0.25 mL of aqueous ammonium hydroxide was added to the slurry to maintain a pH of 8.5-9.0. The mixture was then agitated an additional 10 minutes.

The solution was allowed to cool to room temperature then cooled in an ice bath to 5° C. while agitation was continued. The solid was then filtered, washed with water and dried. The crystals were cube-like particles; approximately 95% of the particles were smaller than 3 microns.

EXAMPLE 7

Crystallization of Omeprazole with Sodium Dodecyl Sulfate

4 Grams of omeprazole was dissolved in 250 mL of methanol at 40° C.; once dissolution was complete, 0.25 mL of concentrated ammonium hydroxide was added to bring the pH of the solution to 8.5-9.0. Approximately 0.5 grams of sodium dodecyl sulfate was then added to the solution. The solution was filtered into a blow can. The blow can outlet was connected to a jet which had a 0.991 mm ID nozzle. A solution of approximately 0.3 grams of sodium dodecyl sulfate in 250 mL of water at 36° C. was charged in a second blow can which was connected to a similar jet nozzle. The jet nozzles were separated by 0.5 inches. Both blow cans were maintained at 36° C.–40° C. prior to release.

The receiving vessel was charged with 250 mL of water, which was warmed to 35° C. 0.3 grams of sodium dodecyl sulfate and 0.45 grams of milled omeprazole were added to the water and the mixture was slowly agitated.

The blow cans were pressurized to approximately 20 psig with regulated nitrogen. The impinging jets of the blow cans were started simultaneously with the flow rates of each stream approximately 0.7 L/minute (linear velocity approximately 15 m/sec.). After the jet mixing was complete, 0.25 mL of aqueous ammonium hydroxide was added to the slurry to maintain a pH of 8.5-9.0. The mixture was then agitated an additional 10 minutes.

The solution was allowed to cool to room temperature then cooled in an ice bath to 5° C. while agitation was continued. The solid was then filtered, washed with water and dried. The crystals were cube-like particles; approximately 95% of the particles were smaller than 3 microns.

What is claimed is:

1. A process for crystallization of an organic pharmaceutical compound comprising contacting one or more jet streams of a feed solution of the organic pharmaceutical compound with one or more jet stream of an anti-solvent, said jet streams impinging to create high turbulence at their point of impact, and each jet stream having sufficient linear velocity to achieve high intensity micromixing of the feed solution and the anti-solvent prior to nucleation, followed by nucleation and the direct production of small crystals, at least 95% of said crystals having a diameter equal to or less than 25 microns.

2. The process of claim 1 wherein at least one of the jet streams comprises a surfactant.

3. The process of claim 1 wherein the pharmaceutical compound is selected from the group consisting of simvastatin, lovastatin, ((5α, 17β)-(1,1-dimethylethyl)-3-oxo-4-azaandrost-1-ene-17-carboxamide), diltiazem malate, 17β-benzoyl-4-aza-5α-androst-1-ene-3-one, 4″-epi-acetylamino-avermectin $B_1$ and [trans-(−)]-2-[[3-methoxy-2-propoxy-5-[tetrahydro-5-(3,4,5-trimethoxyphenyl)-2-furanyl]phenyl]sulfonyl]ethanol.

4. The process of claim 1 wherein each jet stream is independently at a temperature in the range of about 24° C. to 70° C.

5. The process of claim 1 wherein substantially all of said crystals have a diameter equal to or less than 20 microns.

6. A process for crystallization of an organic pharmaceutical compound comprising contacting one or more jet streams of a first feed solution of the organic pharmaceutical compound with one or more jet streams of a second feed solution of the organic pharmaceutical compound, said jet streams impinging to create high turbulence at their point of impact, and each jet stream having sufficient linear velocity to achieve high intensity micromixing of the first and second feed solutions prior to nucleation followed by nucleation and the direct production of small crystals, at least 95% of said crystals having a diameter equal to or less than 25 microns.

7. The process of claim 6 wherein the pharmaceutical compound is selected from the group consisting of simvastatin, lovastatin, ((5α, 17β)-(1,1-dimethylethyl)-3-oxo-4-azaandrost-1-ene-17-carboxamide), diltiazem malate, 17β-benzoyl-4-aza-5α-androst-1-ene-3-one, 4″-epi-acetylamino-avermectin $B_1$ and [trans-(−)]-2-[[3-methoxy-2-propoxy-5-[tetrahydro-5-(3,4,5-trimethoxyphenyl)-2-furanyl]phenyl]sulfonyl]ethanol.

8. The process of claim 6 wherein two jet streams are used and the two jet streams are substantially diametrically opposed to each other, and the hydrodynamic form of each jet stream remains essentially intact up to the point of impingement.

9. The process of claim 6 wherein at least one of the jet streams comprises a surfactant.

10. The process of claim 6 wherein substantially all of said crystals have a diameter equal to or less than 20 microns.

11. A process for crystallization of an organic pharmaceutical compound comprising contacting two opposing jet streams, one jet stream comprising a feed solution of the organic pharmaceutical compound and the other jet stream comprising an anti-solvent, said opposing jet streams impinging to create high turbulence at their point of impact, and each jet stream having sufficient linear velocity to achieve high intensity micromixing of the feed solution and the anti-solvent prior to nucleation, followed by nucleation and the direct production of small crystals, at least 95% of said crystals having a diameter equal to or less than 25 microns.

12. The process of claim 11 wherein the linear velocity of the jet streams is at least about 5 meters/sec.

13. The process of claim 12 wherein the linear velocity is greater than 10 meters/sec.

14. The process of claim 13 wherein the linear velocity is between about 20–25 meters/sec.

15. The process of claim 14 wherein the compound to be crystallized is simvastatin, and the process is conducted in a temperature range of about 55–70° C.

16. The process of claim 15 wherein the feed solution is comprised of simvastatin dissolved in 100% methanol, the anti-solvent is comprised of 100% water, and a 41:59 volumetric ratio of feed solution:anti-solvent is used.

17. The process of claim 15 wherein the temperature is between 60–70° C.

18. The process of claim 13 wherein the compound to be crystallized is (5α,17β)-(1,1-dimethylethyl)-3-oxo-4-azaandrost-1-ene-17-carboxamide and the process is conducted at room temperature.

19. The process of claim 18 wherein the feed solution is comprised of (5α,17β)-(1,1-dimethylethyl)-3-oxo-4-azaandrost-1-ene-17carboxamide dissolved in a 60:40 volumetric ratio of glacial acetic acid:water, the anti-solvent is comprised of 100% water, and a 1:5.5 volumetric ratio of feed solution:anti-solvent is used.

20. The process of claim 13 wherein the compound to be crystallized is lovastatin, and the process is conducted in a temperature range of about 40–58° C.

21. The process of claim 20 wherein the feed solution is comprised of lovastatin dissolved in a 90:10 volumetric ratio of methanol:water, the anti-solvent is comprised of 100% water, and about a 2.6:1 volumetric ratio of feed solution to anti-solvent is used.

22. The process of claim 13 wherein the compound to be crystallized is omeprazole and the process is conducted in temperature range of about 30° to 42° C.

23. The process of claim 22 wherein at least one of the fluids comprises a surfactant.

24. The process of claim 11 wherein at least one of the jet streams comprises a surfactant.

25. The process of claim 11 wherein the organic pharmaceutical compound is selected from the group consisting of simvastatin, lovastatin, ((5α,17β)-(1,1-dimethylethyl)-3-oxo-4-azaandrost-1-ene-17-carboxamide), diltiazem malate, 17β-benzoyl-4-aza-5α-androst-1-ene-3-one, 4″-epi-acetylamino-avermectin $B_1$ and [trans-(−)]-2-[[3-methoxy-2-propoxy-5-[tetrahydro-5-(3,4,5-trimethoxyphenyl)-2-furanyl]phenyl]sulfonyl]ethanol.

26. The process of claim 11 wherein each jet stream is independently at a temperature in the range of about 25° C. to 70° C.

27. The process of claim 11 wherein substantially all of said crystals have a diameter equal to or less than 20 microns.

28. The process of claim 1 wherein the pharmaceutical compound is omeprazole and at least one of the fluids comprises a surfactant.

* * * * *